(12) United States Patent
Shin et al.

(10) Patent No.: US 11,197,903 B2
(45) Date of Patent: Dec. 14, 2021

(54) COMPOSITION CONTAINING A BEAN EXTRACT FOR IMPROVING BLOOD CIRCULATION AND VASCULAR HEALTH AND METHOD FOR IMPROVING BLOOD CIRCULATION AND VASCULAR HEALTH

(71) Applicant: AMOREPACIFIC CORPORATION, Yongsan-gu (KR)

(72) Inventors: Hyun Jung Shin, Seoul (KR); Jin Kwan Kim, Suwon-Si (KR); Chae Wook Kim, Yongin-si (KR); Kyung Mi Joo, Hwaseong-si (KR); Yeon Su Jeong, Yongin-si (KR); Kyung Min Lim, Hwaseong-si (KR); Dae-Bang Seo, Yongin-si (KR); Yung Hyup Joo, Yongin-si (KR); Sang Jun Lee, Seongnam-si (KR); Young-Ho Park, Seoul (KR)

(73) Assignee: AMOREPACIFIC CORPORATION, Seoul (KR)

( * ) Notice: Subject to any disclaimer, the term of this patent is extended or adjusted under 35 U.S.C. 154(b) by 141 days.

(21) Appl. No.: 16/266,658

(22) Filed: Feb. 4, 2019

(65) Prior Publication Data
US 2019/0167745 A1 Jun. 6, 2019

Related U.S. Application Data

(62) Division of application No. 13/322,381, filed as application No. PCT/KR2010/003335 on May 26, 2010, now abandoned.

(30) Foreign Application Priority Data

May 26, 2009 (KR) .......................... 1020090046107

(51) Int. Cl.
*A61K 36/48* (2006.01)
*A23L 2/52* (2006.01)
*A23L 33/105* (2016.01)

(52) U.S. Cl.
CPC .............. *A61K 36/48* (2013.01); *A23L 2/52* (2013.01); *A23L 33/105* (2016.08); *A61K 2236/333* (2013.01)

(58) Field of Classification Search
None
See application file for complete search history.

(56) References Cited

U.S. PATENT DOCUMENTS

| | | | |
|---|---|---|---|
| 5,534,504 A | 7/1996 | Sollevi | |
| 6,001,368 A | 12/1999 | Jenks | |
| 2002/0009509 A1 | 1/2002 | Bombardelli | |
| 2003/0060449 A1 | 3/2003 | Wang et al. | |
| 2008/0145482 A1* | 6/2008 | Li | A61K 36/48 426/46 |

FOREIGN PATENT DOCUMENTS

| | | |
|---|---|---|
| JP | 9-19276 A | 1/1997 |
| JP | 10-23878 A | 1/1998 |
| JP | 2004-238289 A | 8/2004 |
| JP | 2005-523007 A | 8/2005 |
| JP | 2006-016390 A | 1/2006 |
| JP | 2006-225312 A | 8/2006 |
| JP | 2006-249071 A | 9/2006 |
| JP | 2007-106718 A | 4/2007 |
| KR | 10 1999 0066785 A | 8/1999 |
| WO | WO-03/088749 A1 | 10/2003 |
| WO | WO-03/091237 A1 | 11/2003 |

OTHER PUBLICATIONS

Ae Kyoung Lim et al., "Effects of the Soybean Powder with Rich Aglycone Isoflavone on Lipid Metabolism and Antioxidative Activities in Hyperlipidemic Rats", *J. Korean Soc. Food Sci. Nutr.*, 2008, pp. 302-308, vol. 37, No. 3.
Hae-Sook Oh et al., "Isoflave Contents, Antioxidative and Fibrinolytic Activities of Some Commercial Cooking-with-Rice Soybeans", Korean, *J. Food Sci. Technol.*, 2002, pp. 498-504, vol. 34, No. 3.
Hae-Sook Oh et al., "Isoflavone Contents, Antioxidative and Fibrinolytic Activities of Red Bean and Mung Bean", *Korean J. Soc. Food Cookery Sci.*, 2003, vol. 19, No. 3, pp. 263-270.
Kim, Kang-Sung et al., "Composition of Functional Components of Traditional Korean Soybeans", *Food Science and Biotechnology*, vol. 12, No. 2, 2003, pp. 157-160.
Mee-Kyung Shin et al., "Effect of Soybean Powder on Lipid Metabolism and Enzyme Activities in Iduced Hyperlipidemic Rats", *J. East Asian Soc Dietary Life*, 2006, pp. 165-173, vol. 16, No. 2.
R. Hongsheng et al., "Study on Technology of Extracting Soybean Isoflavones form Soybean Residue." *Cereal and Food Industry*, vol. 13, No. 6, pp. 18-21, 2006.

* cited by examiner

*Primary Examiner* — Terry A McKelvey
*Assistant Examiner* — Catheryne Chen
(74) *Attorney, Agent, or Firm* — Blank Rome LLP

(57) ABSTRACT

The present invention relates to a composition containing a bean extract extracted by low-concentration, low-grade alcohol or fractions thereof. The composition exhibits excellent effects in improving blood circulation, improving obesity, and preventing diabetes, hyperlipidemia and the like, and exhibits the effects of alleviating or treating the symptoms of diabetes, hyperlipidemia, and the like. The present invention also relates to a method for improving blood circulation and vascular health.

6 Claims, 9 Drawing Sheets

COMPOSITION CONTAINING A BEAN EXTRACT FOR IMPROVING BLOOD CIRCULATION AND VASCULAR HEALTH AND METHOD FOR IMPROVING BLOOD CIRCULATION AND VASCULAR HEALTH

CROSS-REFERENCE TO RELATED APPLICATIONS

This application is a divisional application of U.S. application Ser. No. 13/322,381, filed Nov. 23, 2011, which is a U.S. national phase of PCT Application No. PCT/KR2010/003335, filed May 26, 2010, which claims the benefit of Korean Patent Application No. 1020090046107, filed May 26, 2009, each of which are hereby incorporated by reference in their entirety.

TECHNICAL FIELD

The present disclosure relates to a composition containing a bean extract for improving blood circulation and vascular health.

Modern people take in more fats with the change in eating habits, but they tend to exercise less and suffer from various stresses. With the change in the dietary lives, various diseases including hypertension, arteriosclerosis and blood circulation disorder are increasing. In particular, the blood circulation disorder is known to cause such symptoms as decline of memory, lethargy, lack of concentration, chronic fatigue, and the like.

Blood circulation refers to the flow of blood in the body in specific directions, and the blood circulation disorder refers to a condition in which the blood vessels become inelastic and cholesterol, etc. is deposited in the inner wall of the blood vessels, leading to narrowing of the blood vessels and interrupting blood circulation.

The diseases caused by the blood circulation disorder include cardiovascular diseases such as hyperlipidemia, arteriosclerosis, myocardial infarction, cerebral thrombosis, etc. Among the cardiovascular diseases, hypertension, arteriosclerosis, heart disease and stroke are one of the most important causes of death in the elderly people.

As such, if the blood circulation disorder is left untreated, it will lead to difficulties in maintaining normal lives and, in severe cases, various types of diseases and even death. Accordingly, it is thought that prevention is more important than treatment of the diseases caused by the blood circulation disorder. Although drugs for cardiovascular diseases are used clinically at present, they are expensive and may cause various side effects.

DISCLOSURE

Technical Problem

Figure 1:
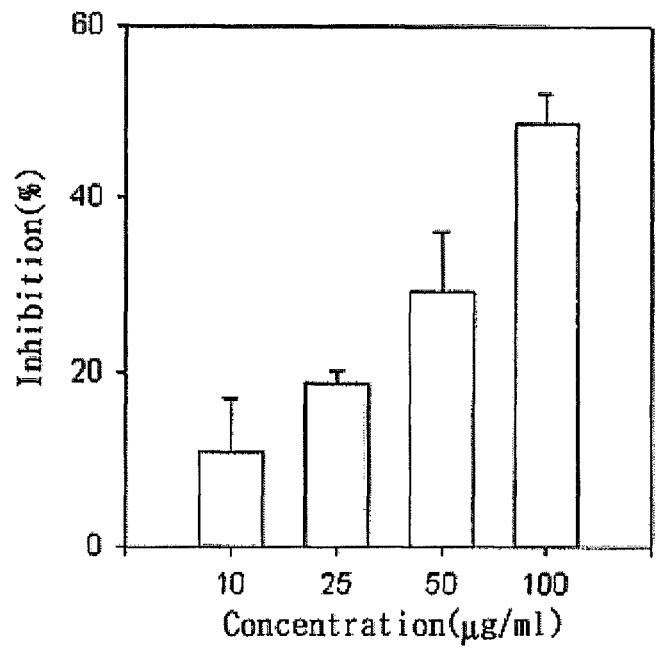
FIG. 1 shows a platelet aggregation inhibition effect of a seoritae extract at different concentrations.

The present disclosure is directed to providing a composition for improving blood circulation.

The present disclosure is also directed to providing a composition for improving vascular health.

The present disclosure is also directed to providing a pharmaceutical composition for improving blood circulation.

The present disclosure is also directed to providing a pharmaceutical composition for improving vascular health.

The present disclosure is also directed to providing a health food composition for improving blood circulation.

The present disclosure is also directed to providing a health food composition for improving vascular health.

Technical Solution

In one general aspect, the present disclosure provides a composition containing a bean extract extracted with a low-concentration, lower alcohol or a fraction thereof as an active ingredient.

Advantageous Effects

The composition according to the present disclosure has superior effect of improving blood circulation and is effective for prevention, amelioration or treatment of cardiovascular diseases, including obesity, diabetes, hyperlipidemia, etc.

BEST MODE

The previous studies on beans are concentrated on isolation and purification of pharmacologically active ingredients from bean, and studies about the medical use of the bean itself are insufficient. In addition, the commonly employed extraction method was one using a high-concentration organic solvent.

A bean extract contains a lot of ingredients not known as yet, and some of them exhibit useful pharmacological effect for the human body. The inventors of the present disclosure have acquired a bean extract using a low-concentration, lower alcohol as extraction solvent, unlike in the extraction method commonly employed for extraction of natural products or herbs, and have shown that the extract exhibits stronger antithrombotic effect than one extracted using a high-concentration organic solvent.

A composition according to an embodiment of the present disclosure comprises a bean extract extracted using a low-concentration organic solvent or a fraction of the extracted bean extract. In an exemplary embodiment, the organic solvent may be a $C_1$-$C_5$ alcohol, although not being limited thereto. The $C_1$-$C_5$ alcohol may be, for example, at least one selected from a group consisting of methanol, ethanol, isopropyl alcohol, n-propyl alcohol, n-butanol and isobutanol, specifically ethanol. In another exemplary embodiment, the concentration of the $C_1$-$C_5$ alcohol may be 1-70% (v/v), specifically 1-40% (v/v), more specifically 5-25% (v/v), more specifically 7-20% (v/v). For example, the solvent may be 10% or 20% (v/v) ethanol.

The composition according to the present disclosure is obtained by extracting bean using the low-concentration, lower alcohol. Through various researches and repeated experiments, the inventors of the present disclosure have identified that a bean extract extracted using a lower alcohol among various organic solvents, for example, ethanol, particularly low-concentration ethanol, has the effect of improving blood circulation and vascular health and thus being useful in alleviation or treatment of obesity, diabetes or hyperlipidemia.

The fraction of the bean extract refers to a component isolated from further fractionation of the bean extract. In an exemplary embodiment, the fraction of the bean extract may be an ethyl acetate or butanol fraction, specifically an ethyl acetate fraction, of the $C_1$-$C_5$ alcohol extract. The inventors of the present disclosure have obtained various fractions from the bean extract extracted using the low-concentration ethanol. As a result, an ethyl acetate or butanol fraction showed better effect of improving blood circulation than a water fraction. Especially, the ethyl acetate fraction showed a very superior effect.

The composition comprising the bean extract or the fraction thereof according to the present disclosure has an effect of inhibiting blood clotting by suppressing platelet aggregation as well as an effect of inducing vasodilation by suppressing constriction of blood vessels. Further, the composition has an effect of reducing lipids in blood and the liver by suppressing increase of cholesterol. Accordingly, the composition is effective in improving blood circulation and vascular health and may be effectively used to treat or prevent obesity, diabetes, hyperlipidemia, or the like.

In an exemplary embodiment, the bean extract or the fraction thereof may comprise adenosine as a marker or functional component. The inventors of the present disclosure have separated and purified the bean extract or the fraction thereof. After measuring activities of the separated and purified products, it was confirmed that adenosine is included therein. In an exemplary embodiment, adenosine may be included in an amount of 0.01-1.0 wt %, more specifically 0.1-0.6 wt %, based on the weight of the bean extract or the fraction thereof. That is to say, the bean extract extracted using the low-concentration, lower alcohol according to the present disclosure contains relatively large amount of active ingredients such as adenosine.

The bean is not particularly limited as long as the bean extract or the fraction thereof has an effect of improving blood circulation. In an exemplary embodiment, the bean may be black bean or colored bean. In another exemplary embodiment, the bean may be at least one selected from a group consisting of Seoritae (*Glycin max* MERR), Seomoktae (*Rhynchosia Nolubilis*), Black soybean (*Glycine max*(L.) Merr), blue bean (*Glycime max* MERR), yellow bean (*Glycime max* MERR), field bean (*Vicia faba*), kidney bean (*Phaseolus vulgaris*), pinto bean (*Phaseolus vulgaris* L.), small red bean (*Vigna angularis*), small black bean (*Phaseolus angularis* .F.WIGHT.), sprouting bean (*Glycine max* (L.) Merr) and soybean (*Glycine max*). More specifically, the bean may be seoritae or field bean.

As used herein the term "black bean" collectively refers to a bean whose grain exhibits black color. The black bean is not particularly limited. For example, it may be black bean (*Glycine max*), Seoritae (*Glycin max* MERR), Seomoktae (*Rhynchosia nolubilis*), Black soybean (*Glycine max*(L.) Merr.), or the like. The black bean may be called differently in different regions. And, the term "black bean extract" collectively refers to a substance extracted from black bean. For example, it includes a substance extracted using an organic solvent and also covers various fractions of the extract.

Also, as used herein the term "colored bean" collectively refers to a bean whose grain exhibits deep color, not only black color but also red, yellow or blue color. Examples of the colored bean include Seoritae (*Glycin* max MERR), Seomoktae (*Rhynchosia nolubilis*), Black soybean (*Glycine max* (L.) Merr.), blue bean (*Glycime max* MERR), yellow bean (*Glycime max* MERR), field bean (*Vicia faba*), kidney bean (*Phaseolus vulgaris*), pinto bean (*Phaseolus vulgaris* L.), small red bean (*Vigna angularis*), small black bean (*Phaseolus angularis* .F.WIGHT.), sprouting bean (*Glycine max* (L.) Merr) and soybean (*Glycine max*), although not being limited thereto. The colored bean may be called differently in different regions. And, the term "colored bean extract" collectively refers to a substance extracted from colored bean. For example, it includes a substance extracted using an organic solvent and also covers various fractions of the extract.

The present disclosure provides a pharmaceutical composition comprising the afore-described composition. In an exemplary embodiment, the pharmaceutical composition may be a pharmaceutical composition for improving blood circulation, preventing cardiovascular disease, or alleviating or treating related symptoms. The pharmaceutical composition according to the present disclosure has the effect of preventing blood clotting, suppressing vasoconstriction and/or reducing cholesterol. Specifically, the pharmaceutical composition may be a pharmaceutical composition for improving blood circulation via antithrombotic effect, or alleviating or treating cardiovascular diseases including obesity, diabetes, hyperlipidemia, etc. The cardiovascular diseases may include, for example, obesity, diabetes, stroke, cerebral hemorrhage, arteriosclerosis, angina, myocardial infarction, hypertension, anemia, migraine, hyperlipidemia, or the like.

When the composition according to the present disclosure is used as a medicine, it may be prepared in the form of solid, semisolid or liquid by adding a commonly used organic or inorganic carrier for oral or parenteral administration.

A formulation for oral administration may be in the form of tablet, pill, granule, soft/hard capsule, powder, fine granule, dust, emulsion, syrup, pellet, or the like. A formulation for parenteral administration may be in the form of injection, drip, ointment, lotion, spray, suspension, emulsion, suppository, or the like. The active ingredient of the present disclosure may be easily prepared into such formulation according to a commonly employed method, and commonly used adjuvants such as surfactant, excipient, colorant, fragrance, preservative, stabilizer, buffering agent, suspending agent, etc. may be adequately used.

The pharmaceutical composition may be administered orally or parenterally, e.g., rectally, topically, transdermally, intravenously, intramuscularly, intraabdominally or subcutaneously.

An administration dose of the active ingredient will vary depending on the age, sex and body weight of the subject, particular disease or pathological condition to be treated, severity of the disease or pathological condition, administration route, or decision by a physician. The determination of the administration dose based on such factors is within the knowledge of those skilled in the art. A general administration dose is 0.001-2000 mg/kg/day, more specifically 0.5-1500 mg/kg/day.

In an exemplary embodiment, the present disclosure provides a food additive, a functional food or a health food comprising the composition according to the present disclosure. Specifically, the composition may be a health food composition for improving blood circulation, or alleviating or treating cardiovascular diseases including obesity, diabetes, hyperlipidemia, etc. The cardiovascular diseases may include, for example, obesity, diabetes, stroke, cerebral hemorrhage, arteriosclerosis, angina, myocardial infarction, hypertension, anemia, migraine, hyperlipidemia, or the like.

The present disclosure provides various types of food additive or functional food comprising the afore-described composition according to the present disclosure. The composition may be processed into fermented milk, cheese, yogurt, juice, probiotic, dietary supplement or other food additives.

In an exemplary embodiment, the composition may further comprise other ingredients providing synergic effect within the range not negatively affecting the main effect desired by the present disclosure. For example, it may further comprise such additives as fragrance, pigment, sterilizer, antioxidant, antiseptic, humectant, thickener, mineral, emulsifier, synthetic polymer, etc. for improvement of physical properties. In addition, it may further comprise such auxiliary ingredients as water-soluble vitamin, oil-soluble vitamin, polypeptide, polysaccharide, seaweed extract, or the like. Those skilled in the art will select and mix these ingredients without difficulty considering the formulation type or purpose of use, and their content may be determined within the range not negatively affecting the purpose and effect of the present disclosure. For example, those ingredients may be added in an amount of 0.01-5 wt %, more specifically 0.01-3 wt %, based on the total weight of the composition.

The composition according to the present disclosure may be in various forms, including solution, emulsion, viscous mixture, tablet, powder, etc., and may be administered in various manners, including drinking, injection, spraying, squeezing, etc.

MODE FOR INVENTION

The examples and experiments will now be described. The following examples and experiments are for illustrative purposes only and not intended to limit the scope of this disclosure.

EXAMPLE 1

Preparation of 10% Ethanol Seoritae (*Glycin Max* MERR) Extract

Dried seoritae (1 kg) was immersed in 10% ethanol solution (10 L) at 50° C. After extracting 3 times for 5 hours under reflux and allowing to stand at room temperature for 12 hours, the extract was filtered, concentrated under reduced pressure and lyophilized to prepare a powder sample. The yield was 7-20% and the prepared powder was kept at low temperature until use.

EXAMPLE 2

Preparation of 20% EAthanol Seoritae (*Glycin Max* MERR) Extract

Dried seoritae (1 kg) was immersed in 20% ethanol solution (10 L) at 50° C. After extracting 3 times for 5 hours under reflux and allowing to stand at room temperature for 12 hours, the extract was filtered, concentrated under reduced pressure and lyophilized to prepare a powder sample. The yield was 7-20% and the prepared powder was kept at low temperature until use.

EXAMPLE 3

Preparation of 50% Ethanol Seoritae (*Glycin Max* MERR) Extract

Dried seoritae (1 kg) was immersed in 50% ethanol solution (10 L) at 50° C. After extracting 3 times for 5 hours under reflux and allowing to stand at room temperature for 12 hours, the extract was filtered, concentrated under reduced pressure and lyophilized to prepare a powder sample. The yield was 7-20% and the prepared powder was kept at low temperature until use.

EXAMPLE 4

Preparation of 70% Ethanol Seoritae (*Glycin Max* MERR) Extract

Dried seoritae (1 kg) was immersed in 70% ethanol solution (10 L) at 50° C. After extracting 3 times for 5 hours under reflux and allowing to stand at room temperature for 12 hours, the extract was filtered, concentrated under reduced pressure and lyophilized to prepare a powder sample. The yield was 7-20% and the prepared powder was kept at low temperature until use.

EXAMPLE 5

Preparation of 20% Ethanol Seomoktae (*Rhynchosia Nolubilis*) Extract

Dried seomoktae (1 kg) was immersed in 20% ethanol solution (5 L) at 60° C. After extracting for 3 hours under reflux and allowing to stand at room temperature for a predetermined time, the extract was filtered, concentrated under reduced pressure and lyophilized to prepare a powder sample. The yield was 3-15% and the prepared powder was kept at low temperature until use.

EXAMPLE 6

Preparation of 20% Ethanol Kidney Bean (*Phaseolus Vulqaris*) Extract

Dried kidney bean (300 g) was immersed in 20% ethanol solution (1.5 L) at 60° C. After extracting for 3 hours under reflux and allowing to stand at room temperature for a predetermined time, the extract was filtered, concentrated under reduced pressure and lyophilized to prepare a powder sample. The yield was 3-15% and the prepared powder was kept at low temperature until use.

EXAMPLE 7

Preparation of 20% Ethanol Pinto Bean (*Phaseolus Vulgaris* L.) Extract

Dried pinto bean (300 g) was immersed in 20% ethanol solution (1.5 L) at 60° C. After extracting for 3 hours under reflux and allowing to stand at room temperature for a predetermined time, the extract was filtered, concentrated under reduced pressure and lyophilized to prepare a powder sample. The yield was 3-15% and the prepared powder was kept at low temperature until use.

EXAMPLE 8

Preparation of 20% Ethanol Sprouting Bean (*Glycine Max* (L.) Merr.) Extract

Dried sprouting bean (300 g) was immersed in 20% ethanol solution (1.5 L) at 60° C. After extracting for 3 hours under reflux and allowing to stand at room temperature for a predetermined time, the extract was filtered, concentrated under reduced pressure and lyophilized to prepare a powder sample. The yield was 3-15% and the prepared powder was kept at low temperature until use.

EXAMPLE 9

Preparation of 20% Ethanol Yellow Bean (*Glycime Max* MERR) Extract

Dried yellow bean (1 kg) was immersed in 20% ethanol solution (5 L) at 60° C. After extracting for 2 times for 3 hours under reflux and allowing to stand at room temperature for a predetermined time, the extract was filtered, concentrated under reduced pressure and lyophilized to prepare a powder sample. The yield was 3-15% and the prepared powder was kept in a refrigerator until use.

EXAMPLE 10

Preparation of 20% Ethanol Blue Bean (*Glycime Max* MERR) Extract

Dried blue bean (300 g) was immersed in 20% ethanol solution (1.5 L) at 60° C. After extracting for 3 hours under reflux and allowing to stand at room temperature for a predetermined time, the extract was filtered, concentrated under reduced pressure and lyophilized to prepare a powder sample. The yield was 3-15% and the prepared powder was kept in a refrigerator until use.

EXAMPLE 11

Preparation of 20% Ethanol Field Bean (*Vicia Faba*) Extract

Dried field bean (1 kg) was immersed in 20% ethanol solution (5 L) at 60° C. After extracting for 3 hours under reflux and allowing to stand at room temperature for a predetermined time, the extract was filtered, concentrated under reduced pressure and lyophilized to prepare a powder sample. The yield was 3-15% and the prepared powder was kept at low temperature until use.

EXAMPLE 12

Preparation of 20% Ethanol Soybean (*Glycine Max*) Extract

Dried soybean (1 kg) was immersed in 20% ethanol solution (5 L) at 60° C. After extracting for 3 hours under reflux and allowing to stand at room temperature for a predetermined time, the extract was filtered, concentrated under reduced pressure and lyophilized to prepare a powder sample. The yield was 3-15% and the prepared powder was kept at low temperature until use.

EXAMPLE 13

Preparation of 20% Ethanol Small Black Bean (*Phaseolus angularis* .F.WIGHT.) Extract Dried geodu (300 g) was immersed in 20% ethanol solution (1.5 L) at 60° C. After extracting for 3 hours under reflux and allowing to stand at room temperature for a predetermined time, the extract was filtered, concentrated under reduced pressure and lyophilized to prepare a powder sample. The yield was 3-15% and the prepared powder was kept in a refrigerator until use.

EXAMPLE 14

Preparation of 20% Ethanol Small Red Bean (*Viona Angularis*) Extract

Dried red bean (300 g) was immersed in 20% ethanol solution (1.5 L) at 60° C. After extracting for 3 hours under reflux and allowing to stand at room temperature for a predetermined time, the extract was filtered, concentrated under reduced pressure and lyophilized to prepare a powder sample. The yield was 3-15% and the prepared powder was kept at low temperature until use.

EXAMPLE 15

Preparation of 20% Ethanol Black Soybean (*Glycine Max* (L.) Merr.) Extract

Dried heuktae (300 g) was immersed in 20% ethanol solution (1.5 L) at 60° C. After extracting for 3 hours under reflux and allowing to stand at room temperature for a predetermined time, the extract was filtered, concentrated under reduced pressure and lyophilized to prepare a powder sample. The yield was 3-15% and the prepared powder was kept at low temperature until use.

EXAMPLE 16

Preparation of Seoritae (*Glycin Max* MERR) Butanol Extract

The 20% ethanol seoritae extract (25 g) obtained in Example 2 was dissolved in distilled water (250 mL). After extracting 2 times with n-butanol (250 mL) using a separatory funnel, the resulting butanol layer was concentrated under reduced pressure and lyophilized to prepare a sample. The yield was 5-15% and the prepared sample was kept in a refrigerator until use.

EXAMPLE 17

Preparation of Seomoktae (*Rhynchosia Nolubilis*) Butanol Extract

The 20% ethanol seomoktae extract (1 g) obtained in Example 5 was dissolved in distilled water (10 mL). After extracting 2 times with n-butanol (10 mL) using a separatory funnel, the resulting butanol layer was concentrated under reduced pressure and lyophilized to prepare a sample. The yield was 5-15% and the prepared sample was kept in a refrigerator until use.

EXAMPLE 18

Preparation of Field Bean (*Vicia Faba*) Butanol Extract

The 20% ethanol field bean extract (25 g) obtained in Example 11 was dissolved in distilled water (250 mL). After extracting 2 times with n-butanol (250 mL) using a separatory funnel, the resulting butanol layer was concentrated under reduced pressure and lyophilized to prepare a sample. The yield was 5-15% and the prepared sample was kept in a refrigerator until use.

EXAMPLE 19

Preparation of Blue Bean (*Glycime Max* MERR) Butanol Extract

The 20% ethanol blue bean extract (1 g) obtained in Example 10 was dissolved in distilled water (10 mL). After extracting 2 times with n-butanol (10 mL) using a separatory funnel, the resulting butanol layer was concentrated under reduced pressure and lyophilized to prepare a sample. The yield was 5-15% and the prepared sample was kept at low temperature until use.

EXAMPLE 20

Preparation of Yellow Bean (*Glycime Max* MERR) Butanol Extract

The 20% ethanol yellow bean extract (1 g) obtained in Example 9 was dissolved in distilled water (10 mL). After extracting 2 times with n-butanol (10 mL) using a separatory funnel, the resulting butanol layer was concentrated under reduced pressure and lyophilized to prepare a sample. The yield was 5-15% and the prepared sample was kept at low temperature until use.

EXAMPLE 21

Preparation of Sprouting Bean (*Glycine Max* (L.) Merr.) Butanol Extract

The 20% ethanol sprouting bean extract (1 g) obtained in Example 8 was dissolved in distilled water (10 mL). After extracting 2 times with n-butanol (10 mL) using a separatory funnel, the resulting butanol layer was concentrated under reduced pressure and lyophilized to prepare a sample. The yield was 5-15% and the prepared sample was kept at low temperature until use.

EXAMPLE 22

Preparation of Soybean (*Glycine Max*) Butanol Extract

The 20% ethanol soybean extract (25 g) obtained in Example 12 was dissolved in distilled water (250 mL). After extracting 2 times with n-butanol (250 mL) using a separatory funnel, the resulting butanol layer was concentrated under reduced pressure and lyophilized to prepare a sample. The yield was 5-15% and the prepared sample was kept at low temperature until use.

EXAMPLE 23

Preparation of Kidney Bean (*Phaseolus Vulgaris*) Butanol Extract

The 20% ethanol kidney bean extract (1 g) obtained in Example 6 was dissolved in distilled water (10 mL). After extracting 2 times with n-butanol (10 mL) using a separatory funnel, the resulting butanol layer was concentrated under reduced pressure and lyophilized to prepare a sample. The yield was 5-15% and the prepared sample was kept at low temperature until use.

EXAMPLE 24

Preparation of Fractions of Seoritae (*Glycin Max* MERR) Extract

Dried seoritae (1 kg) was immersed in 20% ethanol solution (10 L) at 50° C. After extracting 3 times for 5 hours under reflux and allowing to stand at room temperature for 12 hours, the extract was filtered and concentrated under reduced pressure.

After adding 5 times the volume of ethyl acetate solution to the concentrated filtrate and allowing to stand at room so that separation occurs between an ethyl acetate and a water layer, only the ethyl acetate layer was taken and lyophilized to prepare fractions. The prepared powder was kept at low temperature until use.

COMPARATIVE EXAMPLE

Preparation of Seoritae (*Glycin Max* MERR) Extract Using Water

Dried seoritae (1 kg) was immersed in 20% water (10 L) at 100° C. After extracting 3 times for 5 hours under reflux and allowing to stand at room temperature for 12 hours, the extract was filtered, concentrated under reduced pressure and lyophilized to prepare a powder sample. The yield was 7-20% and the prepared powder was kept at low temperature until use.

TEST EXAMPLE 1

Inhibition of Human Platelet Aggregation Induced By Collagen of Seoritae (*Glycin Max* MERR) Extract Experiment was performed as follows in order to compare the activity of the extracts depending on ethanol concentration.

In order to isolate human platelet-rich plasma (hereinafter, PRP), blood was taken from the vein of a healthy man who did not take drugs over 2 weeks using 3.2% sodium citrate as anticoagulant. The blood (150 g) was centrifuged for 15 minutes. After separating the supernatant (PRP), the residue was centrifuged again to separate platelet-poor plasma (hereinafter, PPP). The number of platelets in the separated PRP was counted under an optical microscope, and the PRP was diluted with the PPP such that $3 \times 10^8$ platelets were included per 1 mL.

The platelet aggregation activity was evaluated by measuring the change in absorbance using the lumi-aggregometer (Chrono-Log Co., USA). After adding 100 μg/mL of the seoritae extract to the PRP, followed by incubation in a thermomixer for 10 minutes, the incubated PRP (495 μL) was put in a silicone-coated cuvette for measurement of platelet aggregation and further incubated for 1 minute until the temperature reached 37° C. Then, after adding collagen which induces platelet aggregation with a concentration of 5 μg/mL at which the maximum aggregation is achieved, the reaction was observed for 5 minutes. The result is given in Table 1. In Table 1, the inhibition of platelet aggregation (%) is a value relative to that of the control group treated only with collagen as 0%.

TABLE 1

| | Inhibition of platelet aggregation (%) |
|---|---|
| Water extract | 8.3 ± 2.5 |
| 10% ethanol extract | 74.6 ± 6.4 |
| 20% ethanol extract | 40.1 ± 12.2 |
| 50% ethanol extract | 18.8 ± 10.9 |
| 70% ethanol extract | 12.5 ± 8.4 |

As seen from Table 1, the 10% and 20% ethanol extracts showed better platelet aggregation inhibition effect than other extracts. Especially, the 10% ethanol extract showed the best effect.

Also, an experiment was performed to identify the concentration dependence of the platelet aggregation inhibition effect for the 20% ethanol extract. First, the same experiment was performed as described above after adding the extract at concentrations of 10, 25, 50 and 100 μg/mL. The inhibition of platelet aggregation was evaluated relative to that of the control group treated only with collagen as 0%. As seen from FIG. 1, the 20% ethanol extract showed a concentration-dependent platelet aggregation inhibition effect, demonstrating superior effect against blood clotting.

TEST EXAMPLE 2

Inhibition of Human Platelet Aggregation Induced By Collagen of Field Bean (*Vicia Faba*) Extract Experiment was performed as follows in order to compare the activity of the extracts depending on ethanol concentration.

In order to isolate human PRP, blood was taken from the vein of a healthy man who did not take drugs over 2 weeks using 3.2% sodium citrate as anticoagulant. The blood (150 g) was centrifuged for 15 minutes. After separating the supernatant (PRP), the residue was centrifuged again to separate PPP. The number of platelets in the separated PRP was counted, and the PRP was diluted with the PPP such that $3 \times 10^8$ platelets were included per 1 mL.

The platelet aggregation activity was evaluated by measuring the change in absorbance using the lumi-aggregometer (Chrono-Log Co., USA). After adding 200 mg/mL of the field bean extract to the PRP, which had been incubated in a thermomixer at 37° C. for 2 minutes, followed by incubation for 7 minutes, the incubated PRP (500 μL) was put in a silicone-coated cuvette for measurement of platelet aggregation and further incubated for 3 minutes. Then, after adding collagen which induces platelet aggregation with a concentration of 1-3 μg/mL, i.e. the lowest concentration at which the maximum aggregation is achieved, the reaction was observed for 6 minutes. The result is given in Table 2. In Table 2, the inhibition of platelet aggregation (%) is a value relative to that of the control group treated only with collagen as 0%.

TABLE 2

| | Inhibition of platelet aggregation (%) |
|---|---|
| Water extract | 69.0 |
| 10% ethanol extract | 57.3 |
| 20% ethanol extract | 76.3 |
| 30% ethanol extract | 38.7 |
| 40% ethanol extract | 34.7 |
| 50% ethanol extract | 39.7 |
| 70% ethanol extract | 10.7 |

As seen from Table 2, the 10% and 20% ethanol extracts showed better platelet aggregation inhibition effect than other extracts. Especially, the 20% ethanol extract showed the best platelet aggregation inhibition effect.

TEST EXAMPLE 3

Human Platelet Aggregation Inhibition Effect of Different Beans

Under the 20% ethanol extraction condition showing the best activity, experiment was performed as follows in order to investigate the platelet aggregation inhibition of black bean. All the beans used in the experiment were produced in Korea.

Experiment was performed for seoritae, seomoktae and Black soybean. The beans were extracted in the same manner as in Example 2. In order to investigate the platelet aggregation inhibition effect, experiment was performed using 100 μg/mL bean extract under the same condition as in Test Example 1. The result is given in Table 3.

TABLE 3

| Beans | Inhibition of platelet aggregation (%) |
|---|---|
| Seoritae | 45.31 ± 9.67 |
| Seomoktae | 42.86 ± 11.02 |
| Black soybean | 41.78 ± 8.49 |

As seen from Table 3, the black beans seoritae, seomoktae and heuktae showed high platelet aggregation inhibition effect. Accordingly, it was confirmed that the low-concentration ethanol extracts of seoritae, seomoktae and heuktae have superior platelet aggregation inhibition effect.

TEST EXAMPLE 4

Human Platelet Aggregation Inhibition Effect of Different Beans

Under the 20% ethanol extraction condition showing the best activity, experiment was performed as follows in order to investigate the platelet aggregation inhibition of black bean. All the beans used in the experiment were produced in Korea.

Experiment was performed for small black bean, soybean, seoritae, seomoktae, field bean, kidney bean, small red bean, blue bean, sprouting bean and yellow bean. The beans were extracted in the same manner as described above. In order to investigate the platelet aggregation inhibition effect, experiment was performed using 200 μg/mL bean extract under the same condition as in Test Example 2. The result is given in Table 4.

TABLE 4

| Beans | Inhibition of platelet aggregation (%) |
|---|---|
| Small black bean | 31.0 |
| Soybean | 19.3 |
| Seoritae | 65.3 |
| Field bean | 76.3 |
| Kidney bean | 31.0 |
| Small red bean | 32.0 |
| Blue bean | 16.5 |
| Sprouting bean | 37.5 |
| Yellow bean | 2.5 |

As seen from Table 4, seoritae, seomoktae and field bean showed superior platelet aggregation inhibition effect.

TEST EXAMPLE 5

Inhibition Specificity for Different Causes of Platelet Aggregation

Under the 20% ethanol extraction condition, it was investigated whether the seoritae extract show specific inhibition effect for different causes of platelet aggregation.

It is known that platelet aggregation is induced by collagens which are exposed to the bloodstream when a blood vessel is damaged, ADPs secreted by the platelets, stress by the bloodstream (shear stress; hereinafter, SS), and thrombins. Accordingly, it was investigated whether the 20% low-concentration ethanol seoritae extract has inhibition specificity for collagen, ADP, thrombin and shear stress (SS). The evaluation was performed in the same manner as in Test Example 1. ADP, thrombin or shear stress was applied instead of collagen. The result is given in Table 5.

TABLE 5

|  | Collagen | ADP | Thrombin | Shear stress |
|---|---|---|---|---|
| Inhibition of platelet aggregation (%) | 61.38 ± 10.44 | 8.25 ± 3.10 | 19.61 ± 4.52 | 12.36 ± 3.68 |

As seen from Table 5, the 20% ethanol seoritae extract specifically inhibited platelet aggregation induced by collagen, with little effect of inhibiting platelet aggregation induced by other stimulations, i.e. ADP, thrombin or shear stress.

TEST EXAMPLE 6

Active Substance Expression and Secretion Inhibition Effect After Platelet Aggregation When platelets are coagulated by stimulation such as collagen, they express specific proteins on their surface or secrete specific substances out of cells. Accordingly, it was investigated whether the 20% low-concentration ethanol seoritae extract can reduce the expression of P-selectin and secretion of serotonin into the bloodstream by suppressing platelet aggregation.

After adding the sample to the same PRP as that of Test Example 1, followed by incubation for 10 minutes in an incubator and reaction for 6 minutes after adding 10 μg/mL of collagen, the extract was added to the test tube together with anti-CD42b-PE and anti-CD62P-FITC and allowed to react for 20 minutes in the shade. Then, Tyrode's buffer (500 μL) was added to terminate the reaction.

Measurement was made using a fluorescence-activated cell sorter (FACS; BD Bioscience, USA). The degree of P-selectin expression was determined by measuring the reduction of fluorescence due to the expression of P-selectin. The result is given in Table 6. The inhibition of P-selectin expression is given relative to the fluorescence of the extract-untreated group as 100.

TABLE 6

|  | Treatment concentration (μg/mL) | | | |
|---|---|---|---|---|
|  | 10 | 25 | 50 | 100 |
| Inhibition of P-selectin expression (%) | 13.8 ± 2.3 | 19.8 ± 1.6 | 24.1. ± 2.2 | 36.9 ± 1.9 |

As seen from Table 6, the 20% ethanol seoritae extract decreased the expression of P-selectin on the surface of platelets in a concentration-dependent manner.

The secretion of serotonin was measured using the radioisotope method. After adding 0.5 μCi/mL of $^{14}$C-serotonin (Amersham Bioscience, CFA170) to the same PRP as that of Test Example 1, followed by treatment at 37° C. for 45 minutes and further treatment at 37° C. for 10 minutes after adding the extract, 2 μg/mL of collagen was added and allowed to react for 6 minutes. After terminating the reaction by adding EDTA, centrifugation was carried out at 12000×g for 2 minutes. The quantity of secreted of [$^{14}$C]-serotonin in the supernatant was measured using a liquid scintillation counter (Wallac 1409, Perkin Elmer, USA). The inhibition of serotonin secretion was calculated relative to that of the extract-untreated group as 100. The result is given in Table 7.

TABLE 7

|  | Treatment concentration (μg/mL) | | | |
|---|---|---|---|---|
|  | 10 | 25 | 50 | 100 |
| Inhibition of serotonin secretion (%) | 9.8 ± 2.5 | 17.7 ± 3.2 | 38.0. ± 2.2 | 59.4 ± 1.3 |

As seen from Table 7, the 20% ethanol seoritae extract decreased the secretion of serotonin into the bloodstream in a concentration-dependent manner.

TEST EXAMPLE 7

Inhibition of Blood Clotting In Vein In SD Rat

The blood clotting inhibition effect of the 20% ethanol seoritae extract in vivo was investigated as follows. Male Sprague Dawley (hereinafter, SD) rats weighing 220-250 g were used.

0, 50 or 100 µg/mL of the seoritae extract dissolved in saline (300 µL) was orally administered to the SD rat. 1 hour later, sodium pentobarbital (50 mg/kg) was abdominally administered and the rat was generally anesthetized. After cutting the abdomen open, the adipose tissue was removed so that the caudal vena cava could be seen well. Care was taken to avoid damage to the nearby blood vessels when removing the adipose tissue. A filter paper soaked with 5% $FeCl_3$ solution was put on the caudal vena cava for 5 minutes and then removed. 30 minutes later, the caudal vena cava containing blood clots was ligated at 12 mm length and then incised. After transferring the blood clots to saline, water was removed and the weight was measured. The result is given in FIG. 2.

Figure 2:
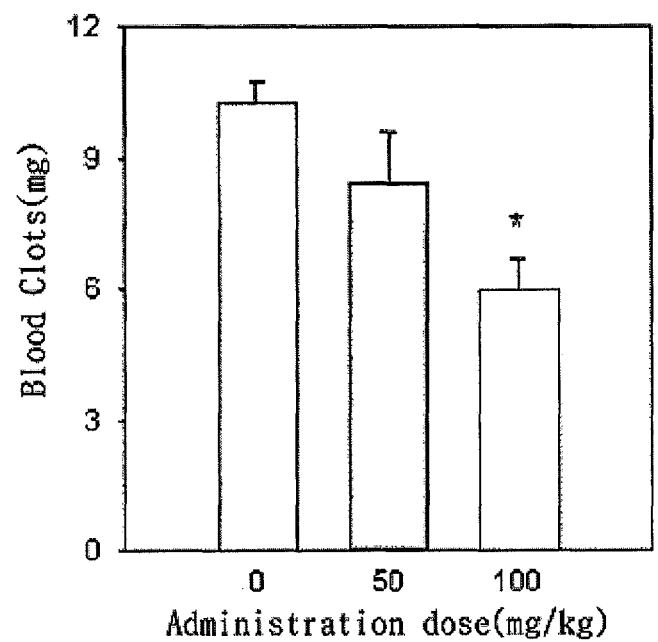
FIG. 2 shows a blood clotting inhibition effect of a seoritae extract when orally administered.

Referring to FIG. 2, it can be seen that the oral administration of the 100 mg/kg seoritae extract significantly inhibits blood clotting.

Figure 3:
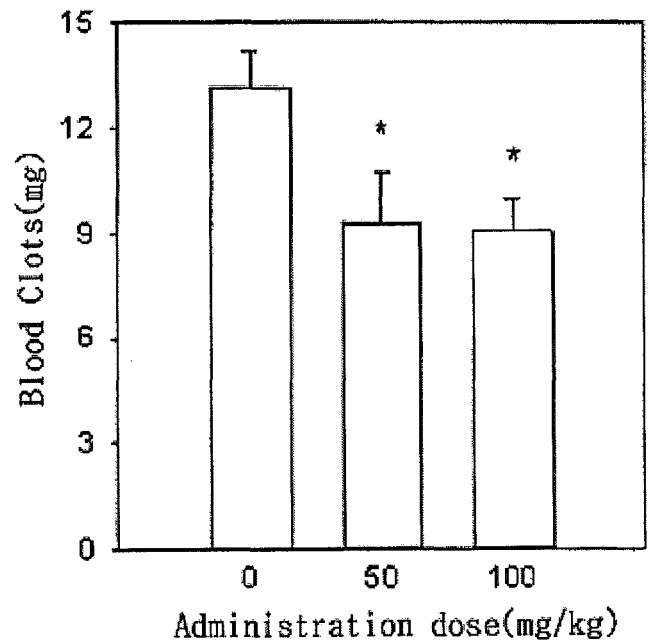
FIG. 3 shows a blood clotting inhibition effect of a seoritae extract when orally administered for 14 days.

Also, the 50 or 100 mg/kg extract was orally administered for 14 days, and the result is shown in FIG. 3. Differently from the result 1 hour after the administration, both the 50 and 100 mg/kg extract significantly inhibited blood clotting. Accordingly, it can be seen that the seoritae extract extracted using the low-concentration ethanol is a superior anticoagulant.

TEST EXAMPLE 8

Human Platelet Aggregation Inhibition Effect of Seoritae Extract

It was investigated which fraction exhibits superior activity under the 20% ethanol extraction condition.

First, ethyl acetate, butanol and water fractions were prepared in the same manner as in Example 25. The platelet aggregation inhibition effect of each fraction (100 µg/mL) was evaluated in the same manner as in Test Example 1. The result is given in Table 8.

TABLE 8

|  | Inhibition of platelet aggregation (%) |
| --- | --- |
| Ethyl acetate fraction | 95.2 ± 0.9 |
| Butanol fraction | 76.8 ± 6.9 |
| Water fraction | 4.7 ± 5.2 |

As seen from Table 8, the ethyl acetate fraction showed the best platelet aggregation inhibition effect, followed by butanol and water fractions. Accordingly, it though that the platelet aggregation inhibition effect of the low-concentration ethanol extract is derived from the active ingredients included in the ethyl acetate fraction.

Figure 4:
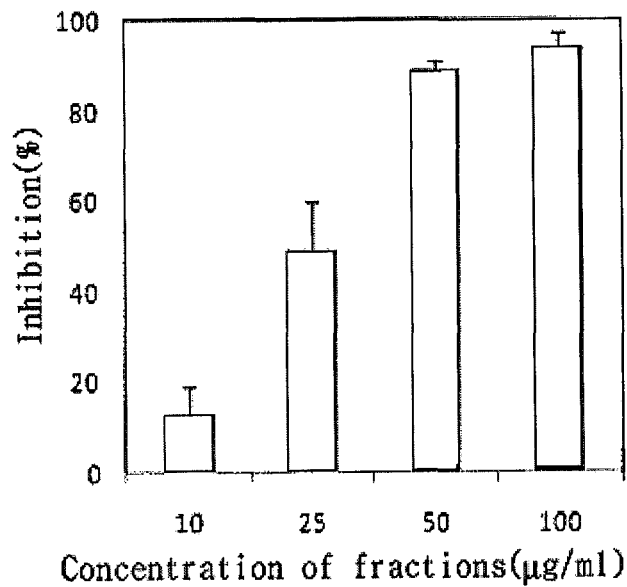
FIG. 4 shows a platelet aggregation inhibition effect of ethyl acetate fractions of a seoritae extract at different concentrations.

In the ethyl acetate fraction that exhibited the best effect, the activity was concentration-dependent, as shown in FIG. 4. That is to say, the platelet aggregation inhibition effect increased in the order of 10, 25, 50 and 100 µg/mL of the ethyl acetate fraction, as seen from FIG. 4.

TEST EXAMPLE 9

Platelet Aggregation Inhibition Effect of Butanol Fractions of Different Beans

Experiment was performed as follows in order to identify the platelet aggregation inhibition effect of the butanol fraction of different beans.

The platelet aggregation inhibition effect of the butanol fraction (200 µg/mL) of soybean, seomoktae, seoritae, field bean, kidney bean, blue bean, sprouting bean and yellow bean was evaluated in the same manner as in Test Example 2. The result is given in Table 9.

TABLE 9

|  | Inhibition of platelet aggregation (%) |
| --- | --- |
| Soybean | 94.0 |
| Seomoktae | 90.5 |
| Seoritae | 72.7 |
| Field bean | 88.5 |
| Kidney bean | 77.5 |
| Blue bean | 91.5 |
| Sprouting bean | 90.5 |
| Yellow bean | 88.5 |

As seen from Table 9, the butanol fractions of all of the beans showed superior platelet aggregation inhibition effect.

TEST EXAMPLE 10

Specificity of Platelet Aggregation Inhibition of Ethyl Acetate Fraction for Different Causes Experiment was performed in the same manner as in Test Example 5 to investigate the specificity of platelet aggregation inhibition of ethyl acetate fractions (50 and 100 µg/mL) for different causes. The result is given in Table 10.

TABLE 10

|  | Conc. | Collagen | ADP | Thrombin | Shear stress |
| --- | --- | --- | --- | --- | --- |
| Inhibition of platelet aggregation (%) | 50 µg/mL | 80.6 ± 0.8 | 25.1 ± 9.2 | 0.6 ± 3.3 | 16.0 ± 2.3 |
|  | 100 µg/mL | 94.0 ± 1.9 | 53.7 ± 6.3 | 9.1 ± 7.7 | 36.9 ± 3.0 |

As seen from Table 10, the ethyl acetate fraction specifically inhibited the activity of collagen in a concentration-dependent manner.

TEST EXAMPLE 11

Inhibition Effect of Ethyl Acetate Fraction Against Expression and Secretion of Active Substances After Platelet Aggregation Experiment was performed in order to investigate the ethyl acetate fraction of seorrtae of reducing expression of P-selectin, secretion of serotonin and generation of thromboxane after platelet aggregation. Experiment for P-selectin and serotonin was performed in the same manner as in Test Example 6. The inhibition of thromboxane generation was evaluated by adding the ethyl acetate fraction to the PRP used in Test Example 1, incubating at 37° C. for 10 minutes, adding collagen (10 µg/mL) and then further incubating for 6 minutes. Some of the sample was added to a test tube containing EDTA and indomethacin (final conc.=50 µM) to terminate the reaction. After centrifuging at 12000×g for 2 minutes, the supernatant was subjected to enzyme immunoassay for quantification of the produced thromboxane.

The inhibition of P-selectin expression by the ethyl acetate fraction is shown Table 11, the inhibition of serotonin secretion in Table 12, and the inhibition of thromboxane generation in Table 13.

TABLE 11

| | Concentration (μg/mL) | | | |
| --- | --- | --- | --- | --- |
| | 10 | 25 | 50 | 100 |
| Inhibition of P-selectin expression (%) | 16.2 ± 2.3 | 39.0 ± 1.5 | 58.8. ± 0.3 | 73.7 ± 0.2 |

TABLE 12

| | Concentration (μg/mL) | | | |
| --- | --- | --- | --- | --- |
| | 10 | 25 | 50 | 100 |
| Inhibition of serotonin secretion (%) | 12.3 ± 2.3 | 40.3 ± 2.0 | 66.8 ± 3.1 | 89.6 ± 0.6 |

TABLE 13

| | Concentration (μg/mL) | | | |
| --- | --- | --- | --- | --- |
| | 10 | 25 | 50 | 100 |
| Inhibition of thromboxane generation (%) | 2.6 ± 0.5 | 5.4 ± 3.7 | 11.4. ± 3.2 | 38.3 ± 3.6 |

As seen from Tables 11, 12 and 13, the ethyl acetate fraction of seoritae reduced the expression of P-selectin, inhibited the secretion of serotonin and inhibited the generation of thromboxane after platelet aggregation, in a concentration-dependent manner.

TEST EXAMPLE 12

Inhibition of Ethyl Acetate Fraction Against Blood Clotting in Vein of SD Rat

Experiment was performed in the same manner as in Test Example 7 in order to investigate whether the administration of the ethyl acetate fraction actually provides blood clotting inhibition effect in vivo. The oral administration dose was 10, 25 and 50 mg/kg, and the amount of produced blood clots was determined 1 hour after the administration. The result is shown in FIG. 5.

Figure 5:
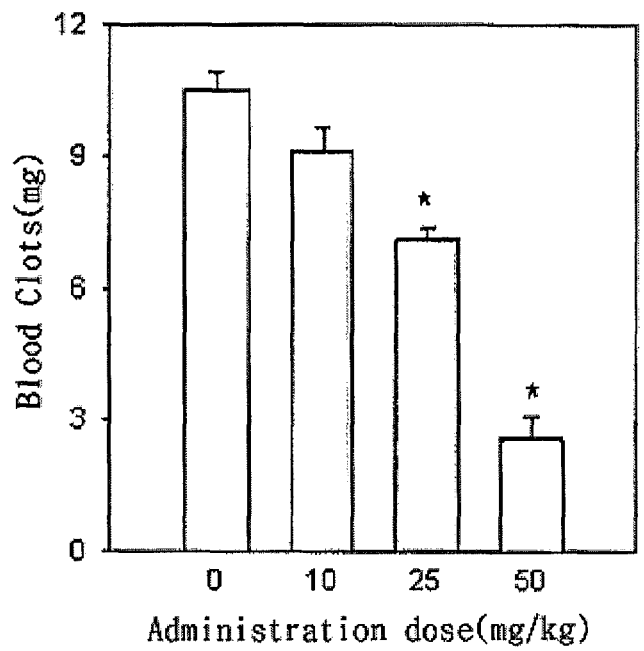
FIG. 5 shows a blood clotting inhibition effect of ethyl acetate fractions of a seoritae extract when orally administered.

As seen from FIG. 5, the oral administration of the ethyl acetate fraction inhibited blood clotting in a concentration-dependent manner.

TEST EXAMPLE 13

Inhibition Effect Against Aggregation of Platelets Derived From SD Rat

Experiment was performed in the same manner as in Test Example 1 in order to investigate whether the low-concentration ethanol extract and the ethyl acetate fraction of seoritae is effective in inhibiting the aggregation of platelets derived from SD rat. The treatment concentration was 10, 25, 50 and 100 μg/mL, and the result is given in Table 14.

TABLE 14

| | | Concentration (μg/mL) | | | |
| --- | --- | --- | --- | --- | --- |
| | | 10 | 25 | 50 | 100 |
| Inhibition of platelet aggregation (%) | Low-concentration extract | 3.7 ± 1.2 | 17.1 ± 2.3 | 36.3 ± 5.7 | 46.5 ± 5.4 |
| | Ethyl acetate fraction | 17.1 ± 6.9 | 48.6 ± 3.8 | 66.1 ± 2.9 | 80.0 ± 4.4 |

As seen from Table 14, not only the ethanol low-concentration extract but also the ethyl acetate fraction showed very superior effect of inhibiting the aggregation of platelets derived from SD rat, in a concentration-dependent manner.

TEST EXAMPLE 14

Observation of Vasoconstriction Inhibition Effect Using Blood Vessel Ring

Male SD rats for experiment weighing 250-300 g were acquired from Daehan Biolink (Seoul, Korea) and kept under the condition of 22±2° C. and 45-55% humidity, with 12/12-hr light/dark cycles (light from 7 a.m. to 7 p.m.). Feed (Purina Korea, Seoul, Korea) and water were given freely during an accommodation period of 1 week.

After sacrificing the rat by bleeding, the chest was cut open and the thoracic aorta was taken out quickly and transferred to KR buffer [composition (mM): NaCl 115.5, KCl 4.6, $KH_2PO_4$ 1.2, $MgSO_4$ 1.2, $CaCl_2$ 2.5, $NaHCO_3$ 25.0, $Ca^{2+}$EDTA 0.026, glucose 11.1; pH 7.4]saturated with 95% $O_2$/5% $CO_2$ mixture gas. A 3-4 mm long blood vessel ring was prepared by removing the blood and neighboring adipose and connective tissues in the blood vessel. After applying tension gradually to the blood vessel ring for initial 30 minutes until the equilibrium was reached, it was constricted with $10^{-6}$ M phenylephrine and then dilated with $10^{-6}$ M acetylcholine. The one with vasodilation of 80% or more was used. Maximum vasoconstriction was induced by replacing the buffer in a water bath with KR buffer containing 90 mM KCl saturated with 95% $O_2$/5% $CO_2$ mixture gas. After pretreating the blood vessel for 30 minutes with the seoritae extract at different concentrations, vasoconstriction was induced in the water bath with phenylephrine of gradually increasing concentrations. The vasoconstriction induced by phenylephrine and 90 mM KCl is shown in Table 15 and Table 16.

TABLE 15

| Phenylephrine concentration (μM) | Control (constriction %) | Seoritae extract (constriction %) |
| --- | --- | --- |
| 0.1 | 15.26 ± 7.04 | 0.39 ± 0.27 |
| 1 | 60.35 ± 4.83 | 16.30 ± 3.44 |
| 10 | 92.13 ± 8.46 | 40.02 ± 7.57 |
| 100 | 97.69 ± 10.54 | 53.68 ± 10.08 |

As seen from Table 15, the vasoconstriction increased with the concentration of the phenylephrine. The treatment with the seoritae extract at 100 μg/mL resulted in a concentration-dependent vasoconstriction inhibition effect.

TABLE 16

|  | Seoritae extract (μg/mL) | | |
|---|---|---|---|
|  | Control | 25 | 50 |
| Constriction (%) | 87.55 ± 16.01 | 70.45 ± 9.56 | 59.6 ± 6.69 |

As seen from Table 16, the treatment with the seoritae extract at 25 and 50 μg/mL resulted in a concentration-dependent vasoconstriction inhibition effect. Accordingly, it can be seen that the 20% ethanol seoritae extract provides very superior vasoconstriction inhibition effect.

TEST EXAMPLE 15

Lowering of Serum and Liver Lipid Levels in Animal Model 8-week-old female rats weighing 250-300 g were kept in polycarbonate cages, 8 heads per cage, maintained at 22±2° C. and 55±15% relative humidity with $^{12}/_{12}$-hr light/dark cycles. Normal diet or high-cholesterol diet was provided and water was given freely.

Fenofibric acid (200 mg/kg) used for treatment of hyperlipidemia was suspended in 1% methyl cellulose (MC) and orally administered as a positive control. The seoritae extract (200 mg/kg) was orally administered once a day for 4 weeks. After fasting for 12 hours, blood sample was taken from the retro-orbital plexus and centrifuged for 10 minutes at 10000 rcf (relative centrifugal force). After the centrifugation, total cholesterol, LDL-cholesterol, HDL-cholesterol and triglyceride levels in the obtained serum were evaluated.

The analysis was performed using an automated hematology analyzer and the Roche diagnostic kit. The result is shown in Table 17 (serum lipids) and Table 18 (liver lipids).

TABLE 17

| (mg/dL) | Normal | Control | Positive control | Seoritae extract |
|---|---|---|---|---|
| Total cholesterol | 114.25 ± 2.41 | 218.57 ± 20.44 | 112.42 ± 13.33 | 156.42 ± 10.21 |
| HDL-cholesterol | 84.85 ± 0.35 | 55.72 ± 3.56 | 87.89 ± 6.84 | 50.35 ± 6.88 |
| LDL-cholesterol | 30.5 ± 6.42 | 134.75 ± 9.41 | 75.34 ± 2.80 | 97.21 ± 10.44 |

As seen from Table 17, the control group rats fed with the high-cholesterol diet for 4 weeks showed about 2 times higher total cholesterol level and about 4.4 times higher LDL-cholesterol level in serum as compared to the normal group. This shows that hyperlipidemia was induced well by the high-cholesterol diet. The group treated with the seoritae extract as well as the high-cholesterol diet showed about 28% decreased total cholesterol level (156.42 mg/dL) and about 28% decreased LDL-cholesterol level as compared to the control group.

TABLE 18

| (μg/mg) | Normal | Control | Positive control | Seoritae extract |
|---|---|---|---|---|
| Total cholesterol | 5.81 ± 0.85 | 27.96 ± 2.46 | 15.43 ± 0.52 | 13.50 ± 7.62 |
| Triglyceride | 199.91 ± 24.33 | 230.35 ± 10.53 | 185.39 ± 23.84 | 172.32 ± 11.16 |

Total cholesterol and triglyceride levels in the liver are shown in Table 18. It was confirmed that fatty liver was induced by the high-cholesterol diet in the control group. The seoritae extract-treated group showed 52% decreased total cholesterol level and 25% decreased triglyceride level. Accordingly, it was confirmed that the seoritae extract has superior effect of improving serum and liver lipid levels in vivo.

TEST EXAMPLE 16

Analysis of Active Ingredient in Seoritae Extract Fractions

In order to analyze the active ingredient of the seoritae extract, assay-guided fractionation was carried out for the ethyl acetate fractions. The overall scheme of isolating and purifying the active ingredient of the ethyl acetate fraction is shown in FIG. 6.

Figure 6:
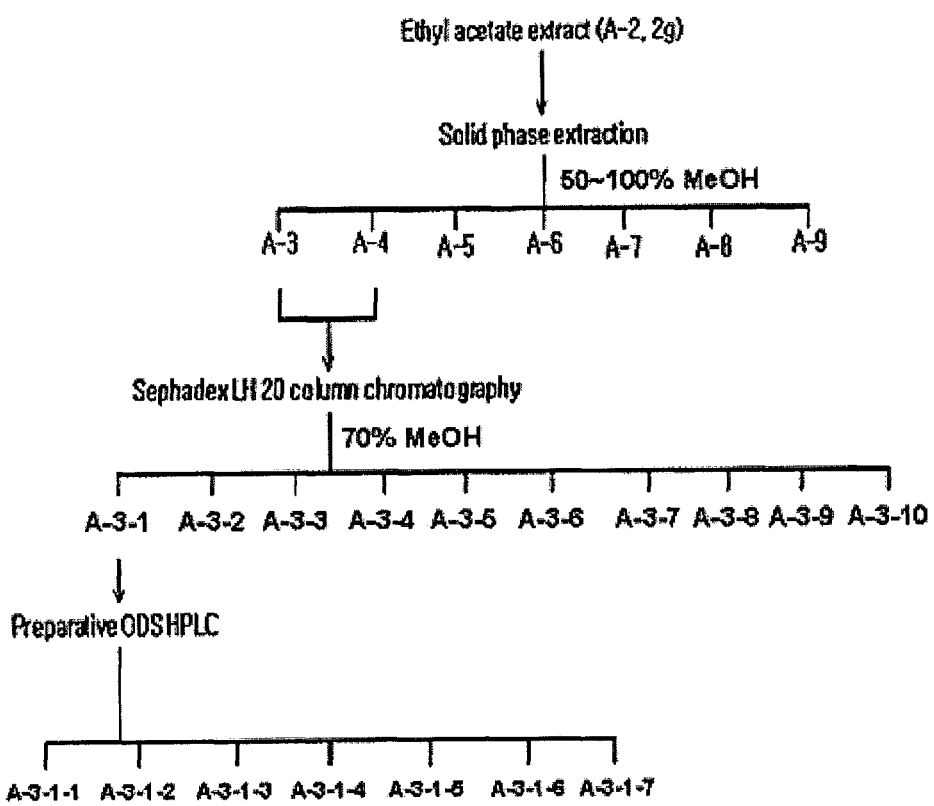
FIG. 6 schematically shows a process of separating and purifying ethyl acetate fractions of a seoritae extract.
Figure 7:
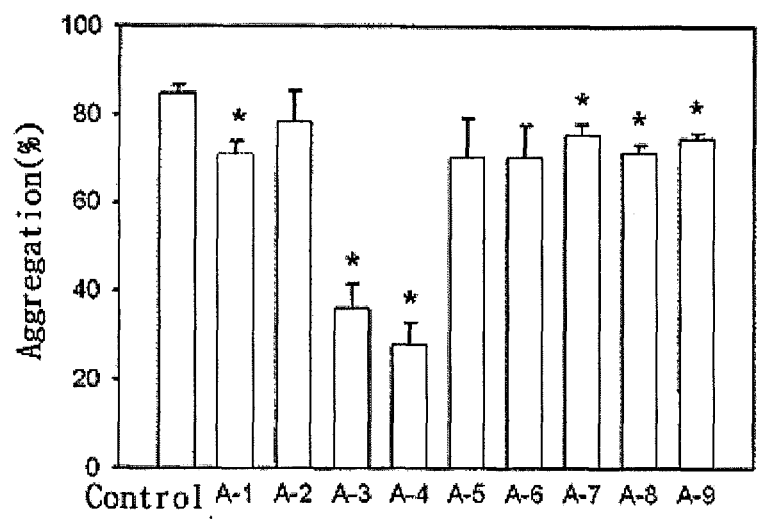
FIGS. 7-9 show a result of measuring platelet aggregation for ethyl acetate fractions of a seoritae extract.

Referring to FIG. 6, solid-phase extraction was carried out for the ethyl acetate fraction A-2 of the 20% ethanol seoritae extract obtained in Example 25. During the solid-phase extraction, 50-100% (v/v) methanol (MeOH) solution was used as the extraction solvent. The solid-phase extracted extract was fractionated to A-3 through A-9. Platelet aggregation was evaluated for the extract, and the result is shown in FIG. 7. As seen from FIG. 7, the extracts A-3 and A-4 showed relatively low platelet aggregation.

Figure 8:
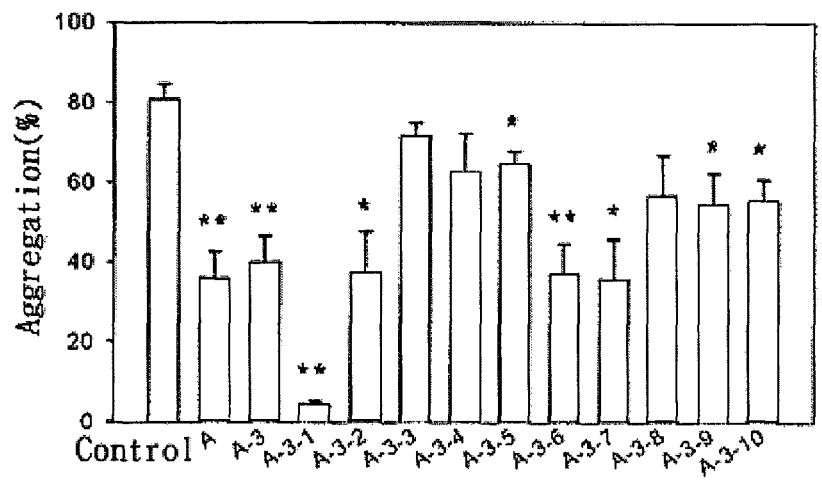

A mixture of the extracts A-3 and A-4 that showed relatively low platelet aggregation was subjected to column chromatography (Sephadex LH 20 column chromatography) for separation of the components. The separated components were numbered from A-3-1 to A-3-10. Platelet aggregation was evaluated again for A-3-1 through A-3-10, and the result is shown in FIG. 8. As seen from FIG. 8, the sample A-3-1 showed the lowest platelet aggregation among A-3-1 through A-3-10.

Figure 9:
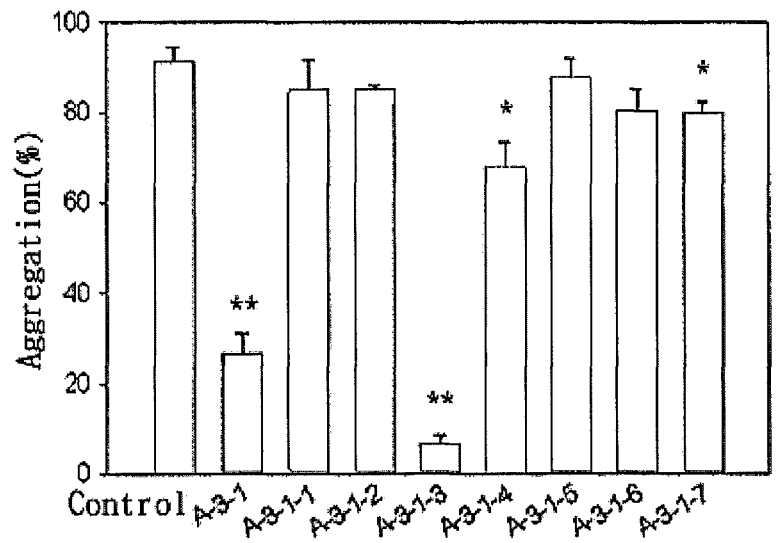

The sample A-3-1 that showed the lowest platelet aggregation was subjected to high-performance liquid chromatography (preparative ODS HPLC) for separation of the active ingredients. The separated components were numbered from A-3-1-1 through A-3-1-7. Platelet aggregation was evaluated for the components, and the result is shown in FIG. 9. As seen from FIG. 9, A-3-1-3 showed the lowest platelet aggregation. To conclude, A-3-1-3 showed the best platelet aggregation inhibition activity.

Figure 10:
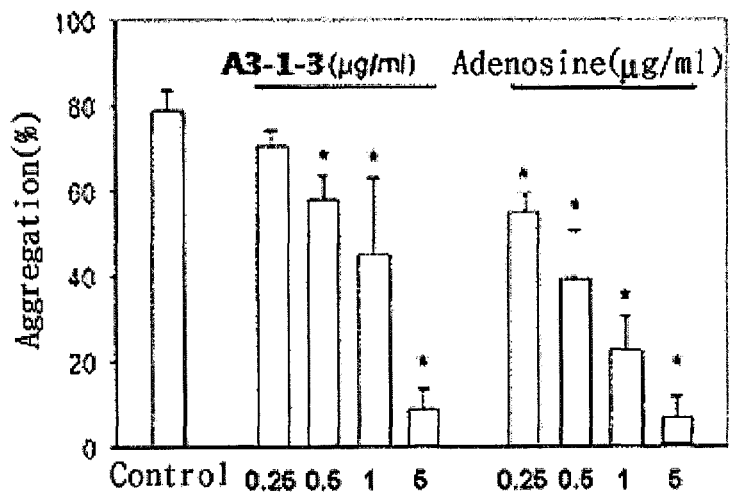
FIG. 10 shows a result of comparing platelet aggregation for a purified ethyl acetate fraction of a seoritae extract with that for adenosine at different concentrations.

The platelet aggregation inhibition activity of A-3-1-3 was compared with that of standard adenosine. The result is shown in FIG. 10. As seen from FIG. 10, A-3-1-3 showed almost the same effect as that of adenosine, suggesting that A-3-1-3 comprises adenosine. The chemical structure of adenosine is as follows:

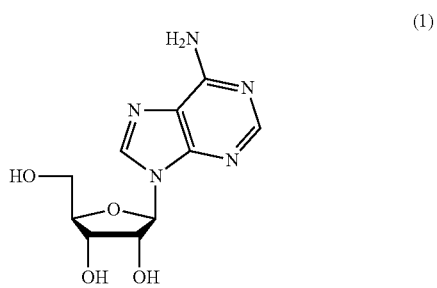

(1)

TEST EXAMPLE 17

Measurement of Adenosine Content in 20% Ethanol Seoritae Extract

Figure 11:
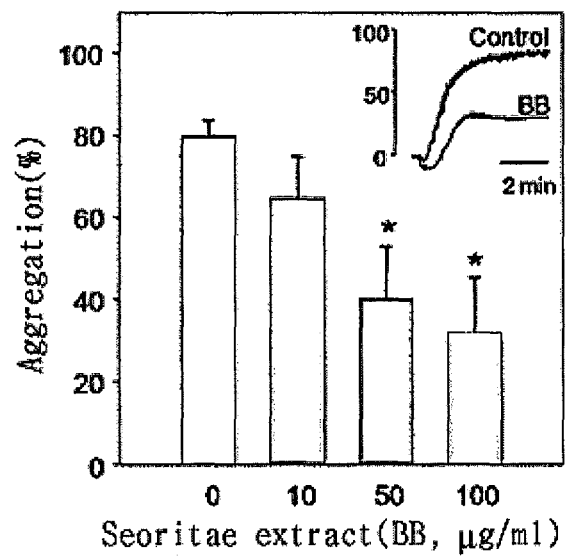
FIG. 11 shows a result of measuring platelet aggregation for a seoritae extract at different concentrations.
Figure 12:
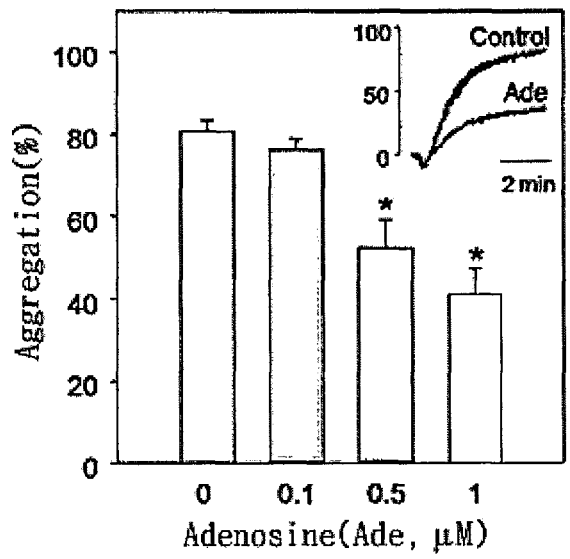
FIG. 12 shows a result of measuring platelet aggregation for adenosine at different concentrations.

The activity of the 20% ethanol seoritae extract was compared with that of standard adenosine, and the result is shown in FIG. 11 and FIG. 12. Referring to FIG. 11 and FIG. 12, the content of adenosine in the 20% ethanol seoritae extract is calculated as 0.35-0.5% from the comparison with the standard adenosine. That is to say, the seoritae extract extracted using the low-concentration, lower alcohol has a very high adenosine content. In addition, the blood clotting inhibition of the seoritae extract is better than that of adenosine alone. Accordingly, a more stable inhibition of blood clotting can be expected from the seoritae extract as compared to when adenosine is used alone.

TEST EXAMPLE 18

Measurement of Adenosine Content in 20% Ethanol Bean Extracts

Adenosine content in the 20% ethanol extracts of various beans including seoritae was measured. The result is given in Table 19.

TABLE 19

| Beans | Adenosine content (%) |
|---|---|
| Seoritae | 0.36 |
| Seomoktae | 0.20 |
| Blue bean | 0.19 |
| Yellow bean | 0.16 |
| Kidney bean | 0.29 |
| Sprouting bean | 0.15 |
| Field bean | 0.34 |

As seen from Table 19, the adenosine content was high with 0.15% or above in various beans. In particular the seoritae and field bean extracts showed relatively high adenosine content.

TEST EXAMPLE 19

Blood Clotting Inhibition Activity of Seoritae (*Glycin Max* MERR) Extract in Red Blood Cells It was investigated whether the bean extract affects the exposure of red blood cells to phosphatidylserine (hereinafter, PS) and the generation of microvesicles (hereinafter, MV) by lysophosphatidic acid (hereinafter, LPA) and phosphatidic acid (hereinafter, PA) which are produced during inflammation.

In general, it is known that blood clotting is facilitated when red blood cells are exposed to PS or MV is generated. After treating with the seoritae extract in inflammatory state, inhibition of PS exposure and MV generation induced by LPA and PA were measured. Specifically, 1 hour after adding the seoritae extract (100 μg/mL), 50 μM LPA or 25 μM PA was added for 15 minutes to induce PS exposure and MV generation. Then, the degree of PS exposure and MV generation was compared between the case where the seoritae extract was treated (+) and untreated (−). The degree of PS exposure is shown in FIG. 13, and the degree of MV generation is shown in FIG. 14.

Figure 13:
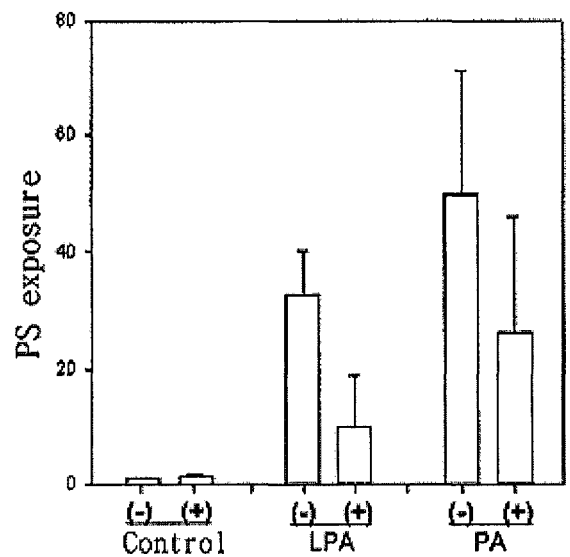
FIG. 13 shows a degree of phosphatidylserine (PS) exposure by lysophosphatidic acid (LPA) or phosphatidic acid (PA) when treated or untreated with a seoritae extract.
Figure 14:
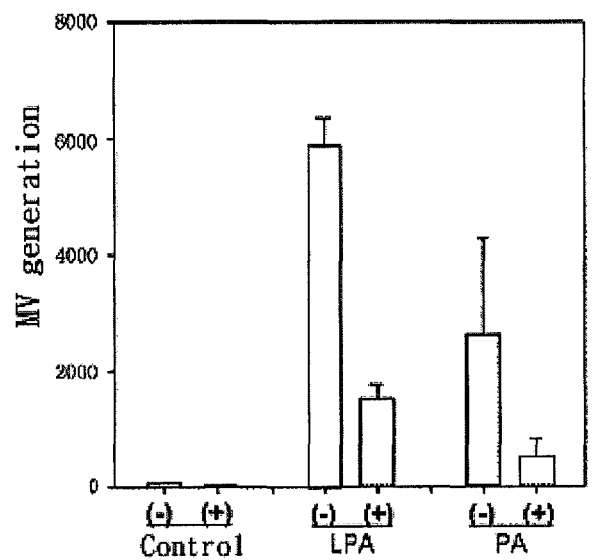
FIG. 14 shows a degree of microvesicle (MV) generation by LPA or PA when treated or untreated with a seoritae extract.

As seen from FIGS. 13 and 14, the seoritae extract inhibited the PS exposure and MV generation induced by LPA and PA.

Figure 15:
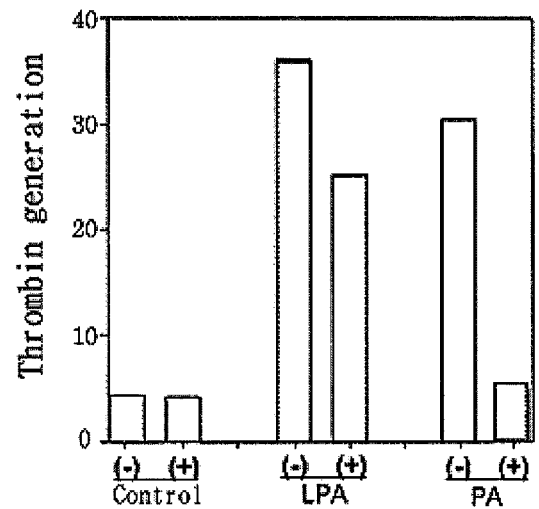
FIG. 15 shows a degree of thrombin generation by LPA or PA when treated or untreated with a seoritae extract.

Further, the degree of thrombin generation was measured by prothrombinase assay from the change in procoagulant activity mediated by PS exposure. The result is shown in FIG. 15. In the figure, (+) is the case where the seoritae extract was treated, and (−) is the case where it was untreated. As seen from FIG. 15, the treatment with the seoritae extract inhibited the thrombin generation by LPA and PA.

TEST EXAMPLE 20

Inhibition of Blood Clotting By Seoritae Extract

Coagulation is a procedure whereby blood clots are formed as coagulation factors which are zymogens are sequentially activated to turn fibrinogen to fibrin. An intrinsic pathway also called the contact system and an extrinsic pathway initiated by the activation of tissue factors lead to the formation of blood clots.

The effect of the 20% ethanol seoritae extract on the extrinsic pathway or the intrinsic pathway of the coagulation cascade was evaluated by the prothrombin time (PT) and the activated partial thromboplastin time (hereinafter, aPTT).

PT was measured as follows. Blood was taken from the rat and centrifuged using 3.8% sodium citrate as anticoagulant. After adding RecombiPlasTin to the supernatant, the time to fibrin formation was measured using a fibrinometer. A longer time means better inhibition of blood clotting.

aPTT was measured as follows. Blood was taken from the rat and centrifuged using 3.8% sodium citrate as anticoagulant. After adding 20 mM calcium chloride ($CaCl_2$) solution to the supernatant, 100 μL of the serum was taken and the time to fibrin formation was measured using a fibrinometer.

Figure 16:
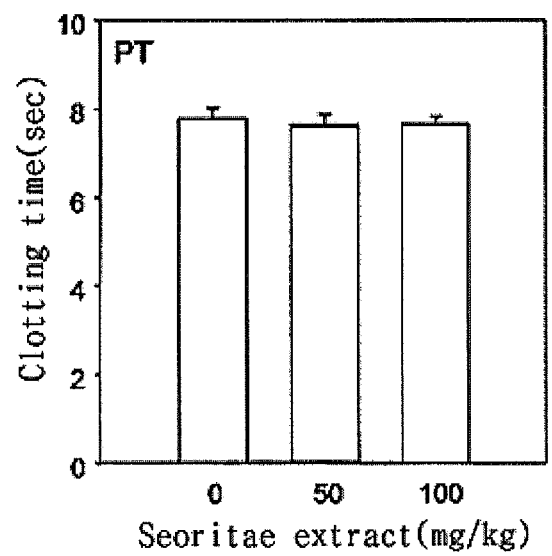
FIGS. 16 and 17 show a result of measuring prothrombin time (PT) and activated partial thromboplastin time (aPTT) after treatment with a seoritae extract at different concentrations.
Figure 17:
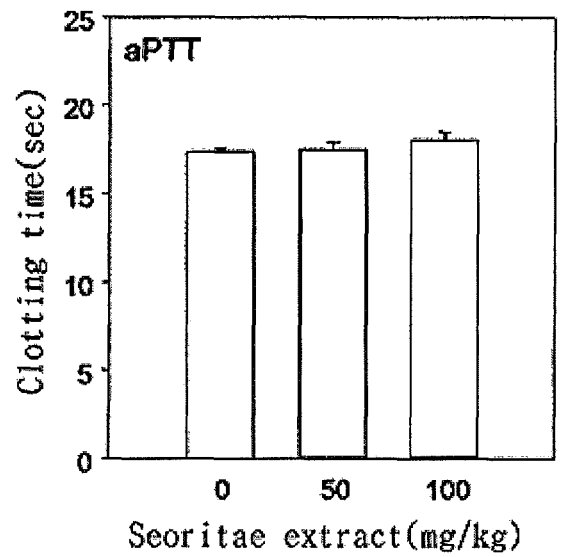

The PT measurement result is shown in FIG. 16, and the aPTT measurement result is shown in FIG. 17.

As seen from FIG. 16 and FIG. 17, the 20% ethanol seoritae extract had no effect on PT or aPTT. Accordingly, since the seoritae extract does not affect the normal coagulation of blood, it will not result in the side effects of the known anticoagulants (e.g., aspirin) such as interruption of hemostasis or excessive bleeding.

TEST EXAMPLE 21

Effect of Seoritae (*Glycin Max* MERR) Extract on Bleeding Time

Bleeding time was compared for the cases where 20% ethanol seoritae extract, aspirin or clopidogrel was treated. The result is shown in FIG. 18.

Figure 18:
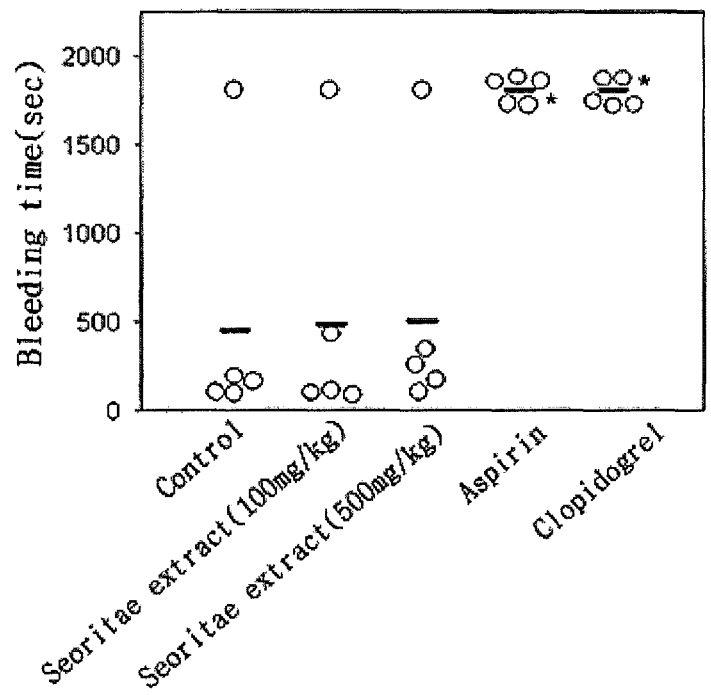
FIG. 18 compares bleeding time when respectively treated with a seoritae extract, aspirin and clopidogrel.

As seen from FIG. 18, aspirin or clopidogrel resulted in significant increase of bleeding time, whereas the seoritae extract resulted in little change in bleeding time. The bleeding time was almost unchanged even when the treatment amount was increased 5-fold from 100 mg/kg to 500 mg/kg. Accordingly, it can be seen that side effects such as increased bleeding time do not occur even when the administration dose or treatment amount is increased.

Hereinafter, the formulation examples of compositions comprising the bean extract according to the present disclosure will be described in detail. The following examples are for illustrative purposes only and not intended to limit the scope of the present disclosure.

FORMULATION EXAMPLE 1

Soft Capsule

Seoritae extract (100 mg) was mixed with soybean extract (50 mg), soybean oil (180 mg), red ginseng extract (50 mg), palm oil (2 mg), hydrogenated palm oil (8 mg), beeswax (4 mg) and lecithin (6 mg), and filled in a soft capsule according to a commonly employed method.

FORMULATION EXAMPLE 2

Tablet

Field bean extract (100 mg) was mixed with soybean extract (50 mg), glucose (100 mg), red ginseng extract (50 mg), starch (96 mg) and magnesium stearate (4 mg). After forming granules by adding 30% ethanol (40 mg), followed by drying at 60° C., a tablet was prepared using a tablet making machine.

FORMULATION EXAMPLE 3

Granule

Seoritae extract (100 mg) was mixed with soybean extract (50 mg), glucose (100 mg), red ginseng extract (50 mg) and starch (600 mg). After forming granules by adding 30% ethanol (100 mg), followed by drying at 60° C., the granules were filled in a pouch. The final weight was 1 g.

FORMULATION EXAMPLE 4

Drink

Seoritae extract (100 mg) was mixed with soybean extract (50 mg), glucose (10 g), red ginseng extract (50 mg), citric acid (2 g) and purified water (187.8 g), and filled in a bottle. The final volume was 200 mL.

FORMULATION EXAMPLE 5

Health Food

| | |
|---|---|
| Seoritae extract | 1000 mg |
| Vitamins | |
| Vitamin A acetate | 70 μg |
| Vitamin E | 1.0 mg |
| Vitamin $B_1$ | 0.13 mg |
| Vitamin $B_2$ | 0.15 mg |
| Vitamin $B_6$ | 0.5 mg |
| Vitamin $B_{12}$ | 0.2 μg |
| Vitamin C | 10 mg |
| Biotin | 10 μg |
| Nicotinamide | 1.7 mg |
| Folic acid | 50 μg |
| Calcium pantothenate | 0.5 mg |
| Minerals | |
| Ferrous sulfate | 1.75 mg |
| Zinc oxide | 0.82 mg |
| Magnesium carbonate | 25.3 mg |
| Potassium phosphate monobasic | 15 mg |
| Calcium phosphate dibasic | 55 mg |
| Potassium citrate | 90 mg |
| Calcium carbonate | 100 mg |
| Magnesium chloride | 24.8 mg |

The exemplary contents of the vitamins and minerals in the health food may be changed as desired. The above ingredients were mixed and prepared into granules according to the commonly employed health food preparation method for use in the preparation of the health food composition.

FORMULATION EXAMPLE 6

Health Drink

| | |
|---|---|
| Field bean extract | 1000 mg |
| Citric acid | 1000 mg |
| Oligosaccharide | 100 g |
| Concentrated plum extract | 2 g |
| Taurine | 1 g |
| Purified water to make | 900 mL |

The above ingredients were mixed and heated at 85° C. for about 1 hour with stirring according to the commonly employed health drink preparation method. The resulting solution was put in a sterilized 2-L container, sealed and sterilized, and then kept in a refrigerator for use in the preparation of the health drink composition.

The composition of the health drink may be changed considering regional or ethnic preferences, such as particular customers, country, purpose of use, or the like.

The composition according to the present disclosure may be widely applicable in the field of medicine, food and others.

The invention claimed is:

1. A method for improving blood circulation of a subject, comprising administering to the subject an effective amount of a bean extract extracted with a $C_1$-$C_5$ alcohol with a concentration of 1-70% (v/v) or a fraction thereof wherein the bean extract or the fraction thereof suppresses blood clotting in the subject,
   wherein the bean is at least one selected from a group consisting of Seoritae, Seomoktae and field bean,
   wherein the bean extract or the fraction thereof comprises adenosine, and
   wherein the adenosine is included in an amount of 0.01-1.0 wt % based on the weight of the bean extract or the fraction thereof.

2. The method according to claim 1, wherein the $C_1$-$C_5$ alcohol is ethanol.

3. The method according to claim 1, wherein the concentration of the $C_1$-$C_5$ alcohol is 5-25% (v/v).

4. The method according to claim 1, wherein the bean extract or the fraction thereof improves vascular health.

5. The method according to claim 1, wherein the blood clotting is a platelet aggregation induced by a collagen.

6. The method according to claim 1, wherein the method is for preventing, alleviating or treating obesity, diabetes, stroke, cerebral hemorrhage, arteriosclerosis, angina, myocardial infarction, hypertension, anemia, migraine or hyperlipidemia.

\* \* \* \* \*